United States Patent [19]

Bouda

[11] 4,353,762
[45] Oct. 12, 1982

[54] METHOD AND APPARATUS FOR CONTINUOUSLY ATTACHING ELASTIC STRANDS TO DISPOSABLE ABSORBENT PRODUCTS

[76] Inventor: Francis J. Bouda, 13319 Centerville Rd., Cleveland, Wis. 53015

[21] Appl. No.: 208,222

[22] Filed: Nov. 19, 1980

[51] Int. Cl.³ .................. A61F 13/16; B32B 31/08
[52] U.S. Cl. .................. 156/164; 128/284; 156/229; 156/289; 156/324; 156/522; 156/549; 156/551
[58] Field of Search .......... 128/284; 156/164, 201, 156/202, 216, 229, 522, 549, 551, 289, 324

[56] References Cited

U.S. PATENT DOCUMENTS

| | | | |
|---|---|---|---|
| 3,860,003 | 1/1975 | Buell | 128/284 |
| 4,050,462 | 9/1977 | Woon et al. | 128/284 |
| 4,081,301 | 3/1978 | Buell | 156/216 |
| 4,227,952 | 10/1980 | Sabee | 156/164 |
| 4,239,578 | 12/1980 | Gore | 156/164 |
| 4,240,866 | 12/1980 | Rega | 156/552 |
| 4,261,782 | 4/1981 | Teed | 156/164 |
| 4,284,454 | 8/1981 | Joa | 156/552 |
| 4,285,747 | 8/1981 | Rega | 156/164 |
| 4,300,967 | 11/1981 | Sigl | 156/164 |

*Primary Examiner*—James J. Bell
*Attorney, Agent, or Firm*—Francis J. Bouda

[57] ABSTRACT

In this invention, a continuous elastic ribbon is fed to a diaper assembly station in a stretched condition while, at the same time, an adhesive is continuously applied to the elastic ribbon. Simultaneously, absorbent batts, as well as webs of moisture-impervious backsheet material and moisture-pervious top-sheet material are fed to the diaper assembly station. Further, and simultaneously, while the webs are traveling to the assembly station, a release medium is applied to one of the said webs in selected areas thereof in a manner so as to overlie predetermined, isolated portions of said stretched, elastic ribbon. At the assembly station, the stretched elastic ribbon is adhered to the moisture-impervious backsheet web along portions of the elastic ribbon which intervene the selected areas of the web where the release medium is located. After the adhesive has set up, the stretched elastic ribbon adheres to the moisture impervious backsheet between the release medium, and the elastic is severed in its unadhered areas, whereupon the unadhered portions become relaxed and inactive without affecting the functionality of the adhered portions in the ultimate assemblage.

7 Claims, 4 Drawing Figures

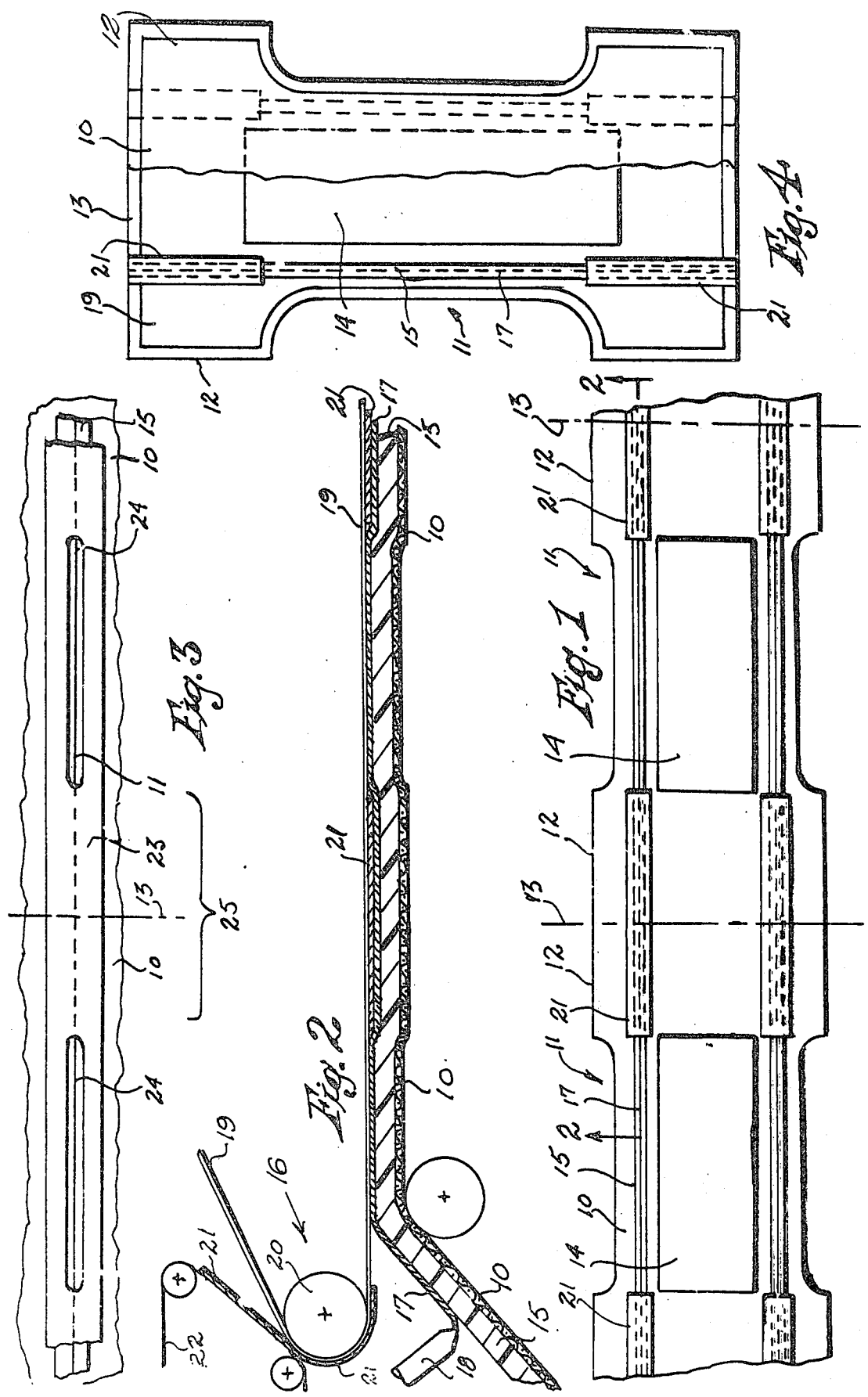

METHOD AND APPARATUS FOR CONTINUOUSLY ATTACHING ELASTIC STRANDS TO DISPOSABLE ABSORBENT PRODUCTS

BACKGROUND OF THE INVENTION

It is well known in the art how to secure an elastic ribbon in a stretched condition to continuously moving webs of material used in garment manufacture as, for instance, to apply an elasticized waistband to underwear, pantyhose, blouses, pants, and the like. Originally, this was done by sewing or by adhesively securing the stretched elastic band in one form or another to the garment.

More recently, the use of such a stretched, elastic band for securing a disposable baby diaper securely in place around the legs of the baby has been shown in issued patents.

U.S. Pat. No. 3,860,003, which issued to Buell on Jan. 14, 1975, shows one form of such "CONTRACTIBLE SIDE PORTIONS FOR DISPOSABLE DIAPER".

Additionally, U.S. Pat. No. 4,081,301, which issued to Buell on Mar. 28, 1978, teaches the METHOD AND APPARATUS FOR CONTINUOUSLY ATTACHING DISCREET, STRETCHED ELASTIC STRANDS TO PREDETERMINE ISOLATED PORTIONS OF DISPOSABLE ABSORBENT PRODUCTS.

The prior art fails, however, to teach how the elastic bands may be applied to the product by continuous application of adhesive to the elastic ribbon or, alternatively, without having to use heat-activated, adhesive coating on the elastic ribbon, said heat-activated, adhesive coating being only selectively activated.

OBJECTS OF THE INVENTION

One object of the present invention is to provide a method and apparatus for joining continuous-stretched bands of elastic in selected, spaced areas at pre-determined points along a continuously-moving, inelastic web.

A further object of the present invention is to provide a method and apparatus for preventing certain portions of the adhesive-plus-elastic band from being secured to selected portions of the inelastic web.

Still a further object of the present invention is to provide a method and apparatus which utilizes a release medium for selectively disassociating the stretched elastic strand from selected portions from the inelastic webs.

SUMMARY OF THE INVENTION

In the present invention, a disposable baby diaper or, in larger form, a disposable absorbent pad for an ambulatory incontinent adult, is manufactured in apparatus and by a process where a web of pervious top cover stock of selected shape is supplied to a similarly-designed impervious web of plastic-backing sheet. Between the two webs, a plurality of absorbent batts or pads are disposed, in spaced relation. Furthermore, in selected portions along the side edges of the webs, generally adjacent to the aforementioned batts, stretched elastic strands are secured to one or both of the webs, while in the stretched condition, by an adhesive which is continuously applied to the full length of the stretched elastic band. At selected areas of the elastic band, a release medium is interposed between the adhesive and adjacent web so that the adhesive secures the elastic strands to a web only in selected portions. Thus the web is separated from those portions of the elastic strand where the elastic strand is not adhered to either of the webs, permitting the unadhered elastic portions to snap back and become relaxed, and also permitting the elastic ribbon in the area attached to the web to contract or gather until the elastic ribbon in that area is relaxed.

With the above and other objects in view, further information and a better understanding of the present invention may be achieved by referring to the following detailed description:

DETAILED DESCRIPTION

For the purpose of illustrating the invention, there is shown in the accompanying drawings a form thereof which is at present preferred, although it is to be understood that the various instrumentalities of which the invention consists can be variously arranged and organized, and that the invention is not limited to the precise arrangement and organizations of the instrumentalities as herein shown and described.

In the drawings, wherein like reference characters indicate like parts:

FIG. 1 is a simplified top plan view of a diaper assembly line, illustrating the absorbent pads, the stretched elastic bands, the release medium, and the severing stations.

FIG. 2 is a vertical cross-sectional view taken generally along line 2—2 of FIG. 1, on a stylized and enlarged scale, indicating how the release medium intervenes one of the inelastic webs and the stretched elastic strand.

FIG. 3 is a fragmentary top plan view showing another form of release strip which can provide the intermittent adhering of a stretched strand to an inelastic web when utilizing a continuously applied strip of adhesive.

FIG. 4 is a top-plan view of a disposable absorbent pad showing how the continuous strip of adhesive secures portions of the stretched elastic strand to the body of the garment while yet not securing the elastic strand to other portions of the garment.

U.S. Pat. Nos. 3,806,003 and 4,081,301, which are hereby incorporated herein by reference, disclose a form of disposable diaper and a method and apparatus for manufacturing one form thereof wherein the diaper has elastically-contractible flexible side portions. It is apparent, however, to those who are skilled in the art and have studied the aforementioned two patents, that the process and apparatus for making the product are extremely complicated because the adhesive for securing the stretched elastic ribbon to the inelastic web material must be either intermittently applied to the stretched, elastic ribbon; or, conversely, if use is made of an elastic ribbon having an heat-activatable adhesive coating on at least one side thereof, such adhesively coated ribbon must be intermittently activated to provide a product shown in the U.S. Pat. No. 3,860,003.

In my invention, the process and apparatus are substantially simplified because the adhesive can be continuously applied to the stretched elastic ribbon, without the need for any selective activation of a ribbon containing heat-activatable adhesive.

Referring now to FIG. 1, I have illustrated a continuous web 10 of inelastic material such as nonwoven cover stock, the kind well known in the construction of disposable baby diapers, sanitary napkins, and the like. This web 10 has portions (along the side thereof) removed, as at 11, to form a shaped or "hour-glass" configuration. The wider ends 12 of the pads are, during the construction of the pad, connected to each other along the line 13, and it is only after the entire pad has been assembled that a suitable cutoff knife (not shown) separates the pad along the severing line 13.

Generally adjacent each of the narrow portions of the web, there is a batt or mat 14 of absorbent material which, in its preferred form, is a comminuted cellulose fluff-like material. However, it is to be understood that this batt 14 may be made of crepe wadding, absorbent tissue, hydrophyllic foam, or any similar absorbent material.

On each side of the web 10, between the batt 14 and the narrowed edge 11, I have secured a stretched elastic strand 15. This strand is applied to the web at the assembly station 16, in a stretched condition and in a manner clearly disclosed in U.S. Pat. No. 4,081,301.

In order to hold the elastic strand 15 in position, I apply a narrow line of glue 17 to one side of the strand 15 by means of the adhesive applicator 18, as is shown more clearly in FIG. 2.

It is preferred that the strip of adhesive 17 be quite narrow so as to be retained completely on the top of the elastic strand 15 without flowing over the sides of said strand.

In order to complete the assembly of the pad, I provide an impervious web 19 which is brought to the assembly station 16 in the manner shown in FIG. 2. This impervious web 19 (which may be a polyethylene plastic sheet) travels around a guide roll 20, so as to overlie the previously described assembly of nonwoven web, elastic strand, batt and adhesive.

Referring now to FIG. 2, I have illustrated how there is applied to one side of the impervious web 19 a release medium 21 which prevents the adhesive from sticking to it or to the impervious web 19. This release medium may be in the form of short strips of release paper, or a continuous strip of release paper having slits or apertures therein, or may be a release medium applied as one of the surface components of the impervious web material 19.

In any event, the release medium is selectively and intermittently applied to selected portions of the web 19 in such a timed relationship that the release medium does not overlie the adhesively-coated elastic strand in the area adjacent the batt 14. This is clearly shown in FIG. 2 where the thickness of the release medium has been exaggerated so that a structure is illustrated whereby the adhesive 17 is kept out of contact with the impervious backing sheet 19 in the pad-end areas 12.

The release medium may be any form of well-known release paper which may be a specially-treated densified Kraft paper or glassine, or other types of paper well known in the manufacture of transfer adhesives, peel-off labels, and the like. This release medium may be provided from rolls (not shown) which unwind as shown at 22 in FIG. 2. It may be applied in either short sections, as shown in FIGS. 1 and 2, or may be a continuous strip as shown at 23 in FIG. 3.

In the event that the continuous strip of release medium is preferred, as at 23, FIG. 3, I form intermittent apertures 24 therein, and it is through these apertures 24 that the adhesive can interconnect the elastic strand 15 to the impervious web 19.

Where the release medium overlies the adhesive, such as in the area generally indicated at 25 in FIG. 3, the adhesive does not come in contact with the impervious backing strip and the elastic strand is free to "snap back" when severed along the cutting line 13.

However, where the apertures 24 are disposed, the adhesive can secure the elastic strand 15 to the impervious web 19.

It is further to be appreciated that instead of applying the release medium in the form of release paper, either intermittently as shown in FIGS. 1 and 2 or as a slotted strip shown at FIG. 3, I may apply a release fluid such as teflon spray or the like, to the impervious backing web, in selected areas, which will then overlie the adhesive-coated elastic strand in the end portions 12 of the assembled pad. This likewise will permit the ends of the stretched elastic strand to "snap back" when the cutting is done along the severing line 13.

Thus it can be seen that I have provided a process and apparatus which enables a stretched elastic strand to be secured to a supporting web in such a manner that portions of said strand are free to "snap back" when the tension of the strand is released, and that all of this simplified procedure can be accomplished without the need for intermittent applications of adhesive or without the need for intermittent activation of an adhesively-coated elastic strand.

It is furthermore to be understood that my present invention may be embodied in other specific forms without departing from the spirit or special attributes; and it is, therefore, desired that the present embodiments be considered in all respects as illustrative and, therefore, not restrictive, reference being made to the appended claims rather than to the foregoing description to indicate the scope of the invention.

Having thus described my invention, what I claim as new and desire to protect by Letters Patent are the following:

1. A method for continuously attaching selected lengths of elastic ribbon to isolated portions of a moving, substantially inelastic web of inter-connected articles to impart an elasticized character to pre-determined isolated portions of said articles, while preserving the substantially inelastic character of said articles in areas where said ribbon is unattached to said web, said method comprising the steps of:

feeding an elastic ribbon to an assembly station in a stretched condition;

continuously applying an adhesive to said stretched elastic ribbon along the length of said ribbon while said stretched elastic ribbon is being fed to said assembly station;

feeding a web of inter-connected articles made with webs of substantially inelastic materials to said assembly station;

applying a release medium to spaced, intermittent portions of one of said substantially inelastic webs;

adhering the stretched, elastic strand to pre-determined, isolated portions of one of said webs in areas which do not have the release medium applied thereto;

maintaining said elastic ribbon in a stretched condition at least until said adhesive sets up;

cutting said elastic ribbon transversely in an area which is not adhered to said web, thereby forming severed, unadhered ends of elastic at both ends of each length of stretched, elastic ribbon adhered to said web;

and allowing the severed, unadhered ends of said elastic ribbon to relax and contract to their unstretched state, whereby said unadhered ends do not impart an elasticized character to said web, nor do they interfere with the functioning of the elasticized portion of the web to which the selected lengths of elastic ribbon are adhered.

2. A method of intermittently attaching an elastic ribbon to pre-determined, isolated portions of at least one of a pair of continuously moving, substantially inelastic, superimposed webs to impart an elasticized character thereto, while preserving the substantially inelastic character thereof in areas where said ribbon is unattached to said web, said method comprising the steps of:

feeding an elastic ribbon to an assembly station in a stretched condition;

continuously applying an adhesive on said stretched elastic ribbon, while said stretched elastic ribbon is being fed to said assembly station;

feeding said first and second webs of substantially inelastic material to said assembly station;

applying a release medium to intermittent spaced portions of one of said webs;

adhering the stretched ribbon to predetermined, selected portions of one of said webs in the areas which do not have the release medium applied thereto;

applying bands of adhesive to at least one of said webs while said webs are being fed to said assembly station, said bands being registered such that they will ultimately lie at the outside of the area occupied by said stretched elastic ribbon, except in those areas where the band of adhesive may overlie the release medium;

adhering said second web to the first web at said assembly station in the areas of said band of adhesive;

maintaining said elastic ribbon in a stretched condition at least until said adhesive on said ribbon sets up;

cutting said webs into separate articles transversely along the line severing said elastic ribbon in a portion of its length passing through the said release medium in a portion of its length which is not adhered to either of said webs; and allowing the severed, unadhered ends of said elastic ribbon to relax and contract to the unstretched length whereby said unadhered ends do not impart any elasticized character to the articles cut from said webs, nor do they interfere with the functioning of elasticized portions of said article to which said elastic ribbon is adhered.

3. The process of claim 1 wherein one of said inelastic webs is an impervious sheet and the other of said webs is a pervious sheet.

4. The process of claim 3 wherein the impervious sheet is polyethylene.

5. The process of claim 3 wherein the pervious web is a nonwoven cover stock material.

6. An apparatus for continuously attaching selected lengths of plastic ribbons to pre-determined isolated portions of a moving substantially inelastic web to impart an elasticized character thereto while preserving a substantially inelastic character of said web in areas where said ribbon is unattached to said web, said apparatus comprising:

means for feeding an elastic ribbon to an assembly station in a stretched condition;

means for continuously applying adhesive to said elastic ribbon at predetermined intervals along the length of said ribbon while said stretched elastic ribbon is being fed to said assembly station;

means for feeding a web of substantially inelastic material to said assembly station;

means for applying a release medium to intermittent portions of one of said webs;

means for adhering the stretched ribbon to predetermined isolated portions of one of said webs in the areas which do not have a release medium applied thereto;

means for maintaining said elastic ribbon in a stretched condition at least until said adhesive sets up;

means for cutting said elastic ribbon transversely in an area which is not adhered to said web, thereby forming severed, unadhered ends of elastic at both ends of each selected length of stretched elastic ribbon adhered to said web.

7. The apparatus of claim 6 wherein the means for cutting the elastic ribbon severs the web along a line passing through the release medium.

* * * * *